US011883490B2

(12) United States Patent
Har-Noy

(10) Patent No.: US 11,883,490 B2
(45) Date of Patent: *Jan. 30, 2024

(54) INDUCTION OF IL-12 USING IMMUNOTHERAPY

(71) Applicant: Mirror Biologics, Inc., Mesa, AZ (US)

(72) Inventor: Michael Har-Noy, Jerusalem (IL)

(73) Assignee: Mirror Biologics, Inc., Wesley Chapel, FL (US)

( * ) Notice: Subject to any disclaimer, the term of this patent is extended or adjusted under 35 U.S.C. 154(b) by 216 days.

This patent is subject to a terminal disclaimer.

(21) Appl. No.: 17/326,009

(22) Filed: May 20, 2021

(65) Prior Publication Data

US 2021/0268106 A1    Sep. 2, 2021

Related U.S. Application Data

(62) Division of application No. 14/962,728, filed on Dec. 8, 2015, now Pat. No. 11,045,541, which is a division of application No. 13/581,745, filed as application No. PCT/US2012/036123 on May 2, 2012, now Pat. No. 9,233,156.

(60) Provisional application No. 61/582,881, filed on Jan. 4, 2012, provisional application No. 61/564,551, filed on Nov. 29, 2011, provisional application No. 61/528,484, filed on Aug. 29, 2011, provisional application No. 61/482,009, filed on May 3, 2011.

(51) Int. Cl.
| | |
|---|---|
| A61K 39/39 | (2006.01) |
| A61K 38/20 | (2006.01) |
| A61K 38/19 | (2006.01) |
| A61K 38/21 | (2006.01) |
| A61K 39/085 | (2006.01) |
| A61K 38/17 | (2006.01) |
| A61K 35/17 | (2015.01) |
| C12N 5/0783 | (2010.01) |
| A61K 39/385 | (2006.01) |
| A61K 39/44 | (2006.01) |
| A61K 39/00 | (2006.01) |

(52) U.S. Cl.
CPC .............. *A61K 39/39* (2013.01); *A61K 35/17* (2013.01); *A61K 38/177* (2013.01); *A61K 38/19* (2013.01); *A61K 38/20* (2013.01); *A61K 38/21* (2013.01); *A61K 39/085* (2013.01); *A61K 39/385* (2013.01); *A61K 39/44* (2013.01); *C12N 5/0637* (2013.01); *A61K 2039/5158* (2013.01); *A61K 2039/55516* (2013.01); *A61K 2039/55522* (2013.01); *A61K 2039/55527* (2013.01); *A61K 2039/55533* (2013.01); *A61K 2039/57* (2013.01)

(58) Field of Classification Search
CPC .................. A61K 39/39; A61K 38/208; A61K 2039/55522; A61K 2039/5158
See application file for complete search history.

(56) References Cited

U.S. PATENT DOCUMENTS

| | | | |
|---|---|---|---|
| 4,279,249 A | 7/1981 | Vert et al. | |
| 5,126,132 A | 6/1992 | Rosenberg | |
| 5,443,983 A | 8/1995 | Ochoa et al. | |
| 5,766,920 A | 6/1998 | Babbitt et al. | |
| 5,806,529 A | 9/1998 | Reisner et al. | |
| 5,846,827 A | 12/1998 | Celis et al. | |
| 6,040,177 A | 3/2000 | Riddell et al. | |
| 6,194,207 B1 | 2/2001 | Bell et al. | |
| 6,251,385 B1 | 6/2001 | Terman | |
| 6,255,073 B1 | 7/2001 | Cai et al. | |
| 6,352,694 B1 | 3/2002 | June et al. | |
| 6,500,193 B1 | 12/2002 | Bezemer et al. | |
| 6,511,511 B1 | 1/2003 | Slivka et al. | |
| 6,514,286 B1 | 2/2003 | Leatherbury et al. | |
| 6,534,055 B1 | 3/2003 | June et al. | |
| 6,572,894 B2 | 6/2003 | Rossling et al. | |
| 6,867,041 B2 | 3/2005 | Berenson et al. | |
| 6,887,466 B2 | 5/2005 | June et al. | |
| 6,905,680 B2 | 6/2005 | June et al. | |
| 6,905,681 B1 | 6/2005 | June et al. | |
| 6,905,874 B2 | 6/2005 | Berenson et al. | |
| 7,402,431 B2 | 7/2008 | Har-Noy | |
| 7,435,592 B2 | 10/2008 | Har-Noy | |
| 7,678,572 B2 | 3/2010 | Har-Noy | |
| 8,354,276 B2 | 1/2013 | Har-Noy | |
| 8,679,841 B2 | 3/2014 | Har-Noy | |
| 8,778,678 B2 | 7/2014 | Har-Noy | |

(Continued)

FOREIGN PATENT DOCUMENTS

| | | |
|---|---|---|
| EP | 0319012 A2 | 6/1989 |
| EP | 2704732 A4 | 2/2015 |

(Continued)

OTHER PUBLICATIONS

Raghupathy, R. et al. (1999). "Maternal Th1- and Th2-Type Reactivity to Placental Antigens in Normal Human Pregnancy and Unexplained Recurrent Spontaneous Abortions." Cellular Immunology, vol. 196, No. 2: pp. 122-130.

Rondon, G., S. Giralt, et al. (1996). "Graft-versus-leukemia effect after allogeneic bone marrow transplantation for chronic lymphocytic leukemia." Bone Marrow Transplant 18(3): 669-72.

Rosenberg, S. A. (2001). "Progress in the development of immunotherapy for the treatment of patients with cancer." Journal of Internal Medicine, vol. 250, No. 6: pp. 462-475.

(Continued)

*Primary Examiner* — Prema M Mertz
(74) *Attorney, Agent, or Firm* — Westman, Champlin & Koehler, P.A.; Z. Peter Sawicki

(57) ABSTRACT

The present invention relates to compositions and methods that promote the induction of IL-12 in a patient. The composition includes activated allogeneic cells that are administered to a patient with a disease such as cancer. Administration of the composition skews the patient's immune response to a Th1 environment and produces detectable levels of IL-12 in the patient's plasma, without any IL-12 related toxicity.

3 Claims, 1 Drawing Sheet

(56) References Cited

U.S. PATENT DOCUMENTS

| | | |
|---|---|---|
| 9,233,156 B2 | 1/2016 | Har-Noy |
| 9,272,001 B2 | 3/2016 | Har-Noy |
| 2002/0127208 A1 | 9/2002 | Waller et al. |
| 2003/0004578 A1 | 1/2003 | Brown et al. |
| 2003/0134415 A1 | 7/2003 | Gruenberg |
| 2003/0175272 A1 | 9/2003 | Gruenberg |
| 2003/0215946 A1 | 11/2003 | Nair et al. |
| 2004/0228848 A1 | 11/2004 | Har-Noy |
| 2005/0065593 A1 | 3/2005 | Chu et al. |
| 2005/0191746 A1 | 9/2005 | Van et al. |
| 2006/0036331 A1 | 2/2006 | Lu et al. |
| 2006/0115487 A1 | 6/2006 | Har-Noy |
| 2006/0121021 A1 | 6/2006 | Hunig |
| 2007/0086996 A1 | 4/2007 | Har-Noy |
| 2008/0112963 A1 | 5/2008 | Har-Noy |
| 2008/0112975 A1 | 5/2008 | Har-Noy |
| 2016/0089433 A1 | 3/2016 | Har-Noy |

FOREIGN PATENT DOCUMENTS

| | | |
|---|---|---|
| JP | 9255577 | 9/1997 |
| JP | 2007500217 A | 5/2003 |
| JP | 2010509337 A | 3/2010 |
| JP | 2010-536330 A | 12/2010 |
| WO | 9412196 A1 | 6/1994 |
| WO | 9746256 A1 | 12/1997 |
| WO | 9924045 A1 | 5/1999 |
| WO | 0162092 A1 | 8/2001 |
| WO | 200162895 A2 | 8/2001 |
| WO | 2003024989 | 3/2003 |
| WO | 2003038062 | 10/2003 |
| WO | 2004004768 A1 | 1/2004 |
| WO | 2005001074 A | 1/2005 |
| WO | 2005081982 A | 9/2005 |
| WO | 2005084276 A | 9/2005 |
| WO | 2007120128 A1 | 10/2007 |
| WO | 2009135199 A2 | 11/2009 |
| WO | 2011084451 A2 | 7/2011 |
| WO | 2012151279 A3 | 12/2012 |

OTHER PUBLICATIONS

Roussel, E. et al. (1996). "Predominance of a type 2 intratumoural immune response in fresh tumour-infiltrating lymphocytes from human gliomas." Clinical and Experimental Immunology, vol. 105, No. 2: pp. 344-352.

Rubbi, C.P. et al. (1993). "Evidence of surface antigen detachment during incubation of cells with immunomagnetic beads." Journal of Immunology Methods, vol. 166, No. 2: pp. 233-241.

Santin, A. D. et al. (2000). "Interleukin-10 Increases Th1 Cytokine Production and Cytotoxic Potential in Human Papillomavirus-Specific CD8(+) Cytotoxic T Lymphocytes." Journal of Virology, vol. 74, No. 10: pp. 4729-4737.

Sato, M., S. Goto, et al. (1998). "Impaired production of Th1 cytokines and increased frequency of Th2 subsets in PBMC from advanced cancer patients." Anticancer Res 18(5D): 3951-5.

Saxton, M. L. et al. (1997). "Adoptive Transfer of Anti-CD3-Activated CD4+ T Cells Plus Cyclophosphamide and Liposome-Encapsulated Interleukin-2 Cure Murine MC-38 and 3LL Tumors and Establish Tumor-Specific Immunity." Blood, vol. 89, No. 7: pp. 2529-2536.

Shibuya, T.Y et al. (2000). "Anti-CD3/Anti-CD28 Bead Stimulation Overcomes CD3 Unresponsiveness in Patients With Head and Neck Squamous Cell Carcinoma." Arch Otolaryngol Head Neck Surg, vol. 126, No. 4: 473-479.

Shinomiya, Y., M. Harada, et al. (1995). "Anti-metastatic activity induced by the in vivo activation of purified protein derivative (PPD)-recognizing Th1 type CD4+ T cells." Immunobiology 193(5): 439-55.

Shurin, M. R., L. Lu, et al. (1999). "Th1/Th2 balance in cancer, transplantation and pregnancy." Springer Semin Immunopathol 21(3): 339-59.

Slavin, S. et al. (2001). "Non-myeloablative allogeneic Stem cell transplantation focusing on immunotherapy of life-threatening malignant and non-malignant diseases." Critical Reviews Oncology Hematology, vol. 39, No. 1-2: pp. 25-29.

Slavin, S. et al. (1995). "Allogeneic cell therapy for relapsed leukemia after bone marrow transplantation with donor peripheral blood lymphocytes." Experimental Hematology, vol. 23, No. 14: pp. 1553-1562.

Slavin, S. et al. (1996). "Allogeneic Cell Therapy With Donor Peripheral Blood Cells and Recombinant Human Interleukin-2 to Treat Leukemia Relapse After Allogeneic Bone Marrow Transplantation." Blood, vol. 87, No. 6: pp. 2195-1204.

Slavin, S. et al. (1996). "Allogeneic Cell Therapy: The Treatment of Choice for All Hematologic Malignancies Relapsing Post BMT." Blood, vol. 87, No. 9: pp. 4011-4013.

Slavin, S. et al. (2001). "Nonmyeloablative stem cell transplantation for the treatment of cancer and life-threatening nonmalignant disorders: past accomplishments and future goals." Cancer Chemother Pharmacol, vol. 48, (Suppl 1): pp. S79-S84.

Slavin, S. et al. (1998). "Immunotherapy in conjunction with autologous and allogeneic blood or marrow transplantation in lymphoma." Annals of Oncology, vol. 9 (Suppl 1): pp. S31-S39.

Smith, D. R., S. L. Kunkel, et al. (1994). "Production of interleukin-10 by human bronchogenic carcinoma." Am J Pathol 145(1): 18-25.

Smyth, M. J. et al. (2002). "New Aspects of Natural-Killer-Cell Surveillance and Therapy of Cancer." Nature Reviews Cancer, vol. 2, No. 11: pp. 850-861.

Sredni, B. et al. (1995). "Bone Marrow-Sparing and Prevention of Alopecia by AS101 in Non-Small-Cell Lung Cancer Patients Treated with Carboplatin and Etoposide." Journal of Clinical Oncology, vol. 13, No. 9: pp. 2342-2353.

Sredni, B. et al. (1996). "Predominance of TH1 Response in Tumor-Bearing Mice and Cancer Patients Treated with AS101." National Journal of Cancer Institute, vol. 88, No. 18: pp. 1276-1284.

Sredni, B., R. H. Xu, et al. (1996). "The protective role of the immunomodulator AS101 against chemotherapy-induced alopecia studies on human and animal models." Int J Cancer 65(1): 97-103.

Stein, G., W. Henn, et al. (1998). "Modulation of the cellular and humoral immune responses of tumor patients by mistletoe therapy." Eur J Med Res 3(4): 194-202.

Stern, B. V. et al. (2002). "Vaccination with Tumor Peptide in CpG Adjuvant Protects Via IFN-Gamma-Dependent CD4 Cell Immunity." The Journal of Immunology, vol. 168, No. 12: pp. 6099-6105.

Tabata, T. et al. (1999). "Th2 Subset Dominance Among Peripheral Blood T Lymphocytes in Patients with Digestive Cancers." American Journal of Surgery, vol. 177, No. 3: pp. 203-208.

Taga, K. et al. (1993). "Human Interleukin-10 Can Directly Inhibit T-Cell Growth." Blood, vol. 81, No. 11: pp. 2964-2971.

Takeuchi, T. et al. (1997). "Th2-like response and antitumor effect of anti-interleukin-4 mAb in mice bearing renal cell carcinoma." Cancer Immunol Immunother, vol. 43, No. 6: pp. 375-381.

Tanaka, K., K. Kemmotsu, et al. (1998). "[Flow cytometric analysis of helper T cell subsets (Th1 and Th2) in healthy adults]." Rinsho Byori 46(12): 1247-51.

Tanaka, J., M. Imamura, et al. (1997). "The important balance between cytokines derived from type 1 and type 2 helper T cells in the control of graft-versus-host disease." Bone Marrow Transplant 19(6): 571-6.

Tatsumi, T. et al. (2002). "Disease-associated bias in T helper type 1 (Th1)/Th2 CD4(+) T cell responses against MAGE-6 in HLA-DRB10401 (+) patients with renal cell carcinoma or melanoma." Journal of Experimental Medicine, vol. 196, No. 5: pp. 619-628.

Terao, H., M. Harada, et al. (1994). "Th1 type CD4+ T cells may be a potent effector against poorly immunogenic syngeneic tumors." Biotherapy 8(2): 143-51.

Tessmar, J. et al. (2003). "The use of poly(ethylene glycol)-block-poly(lactic acid) derived copolymers for the rapid creation of biomimetic surfaces." Biomaterials, vol. 24, No. 24: pp. 4475-4486.

Thanhauser, A., A. Bohle, et al. (1995). "The induction of bacillus-Calmette-Guerin-activated killer cells requires the presence of monocytes and T-helper type-1 cells." Cancer Immunol Immunother 40(2): 103-8.

(56) References Cited

OTHER PUBLICATIONS

Thomas, A. K. et al. (2002). "A Cell-Based Artificial Antigen-Presenting Cell Coated with Anti-CD3 and CD28 Antibodies Enables Rapid Expansion and Long-Term Growth of CD4 T Lymphocytes." Clinical Immunology, vol. 105, No. 3: pp. 259-272.
Thomas, E., R. Storb, et al. (1975). "Bone-marrow transplantation (first of two parts)." N Engl J Med 292(16): 832-43.
Thomas, E. D., R. Storb, et al. (1975). "Bone-marrow transplantation (second of two parts)." N Engl J Med 292(17): 895-902.
Tilg, H. et al. (1994). "Interleukin-6 (IL-6) as an Anti-inflammatory Cytokine: Induction of Circulating IL-1 Receptor Antagonist and Soluble Tumor Necrosis Factor Receptor p55." Blood, vol. 83, No. 1: pp. 113-118.
To, W. C. et al. (2000). "Therapeutic Efficacy of Th1 and Th2 L-selectin—CD4+ Tumor-Reactive T Cells." Laryngoscope vol. 110, (10 Pt 1): pp. 1648-1654.
Ueno, N. T., G. Rondon, et al. (1998). "Allogeneic peripheral-blood progenitor-cell transplantation for poor-risk patients with metastatic breast cancer." J Clin Oncol 16(3): 986-93.
Van Besien, K., P. Thall, et al. (1997). "Allogeneic transplantation for recurrent or refractory non-Hodgkin's lymphoma with poor prognostic features after conditioning with thiotepa, busulfan, and cyclophosphamide: experience in 44 consecutive patients." Biol Blood Marrow Transplant 3(3): 150-6.
Voutsadakis, I. A. (2003). "NK cells in allogeneic bone marrow transplantation." Cancer Immunol Immunother, vol. 52, No. 9: pp. 525-534.
Vowels, B. R. et al. (1994). "Th2 Cytokine mRNA Expression in Skin in Cutaneous T-Cell Lymphoma." The Journal of Investigative Dermatology, vol. 103, No. 5: pp. 669-673.
Wang, Q. et al. (1995). "Selective Cytokine Gene Expression in Renal Cell Carcinoma Tumor Cells and Tumor-Infiltrating Lymphocytes." International Journal of Cancer, vol. 61, No. 6: pp. 780-785.
Weber, K., U. Mengs, et al. (1998). "Effects of a standardized mistletoe preparation on metastatic B16 melanoma colonization in murine lungs." Arzneimittelforschung 48(5): 497-502.
Weiden, P. L. et al. (1981). "Antileukemic Effect of Chronic Graft-Versus-Host Disease: Contribution to Improved Survival After Allogeneic Marrow Transplantation." New England Journal of Medicine, vol. 304 No. 25: pp. 1529-1533.
Whitmore, M. et al. (1999). "LPD lipopolyplex initiates a potent cytokine response and inhibits tumor growth." Gene Therapy, vol. 6, No. 11: pp. 1867-1875.
Wong, B. R. et al. (1999). "TRANCE is a TNF family member that regulates dendritic cell and osteoclast function." Journal of Leukocyte Biology, vol. 65, No. 6: pp. 715-724.
Woo, E. Y. et al. (2001). "Regulatory CD4(+)CD25(+) T Cells in Tumors from Patients with Early-Stage Non-Small Cell Lung Cancer and Late-Stage Ovarian Cancer." Cancer Research, vol. 61, No. 12: pp. 4766-4772.
Woo, E. Y. et al. (2002). "Cutting edge: Regulatory T Cells from Lung Cancer Patients Directly Inhibit Autologous T cell proliferation." J Immunol 168(9): 4272-6.
Yamamura, M. (1992). "Defining protective responses to pathogens: cytokine profiles in leprosy lesions." Science 255 (5040): 12.
Office Action issued in corresponding Chinese Patent Application No. 201910193492.3 dated Apr. 13, 2022.
Tang, Y. et al. "Relationship between the Th1/Th2Cytokines Imbalance and Autoimmune Thyroid Diseases" Journal of Chinese Physician, Jul. 2005, vol. 7, No. 7, with English abstract.
Gao, S. et al. "New Breakthrough In Research of Dendritic Cells—induction of immune tolerance" Medical Recapitulate, Aug. 2006, vol. 12, No. 15, with English abstract.
Antin, J. H. et al. (1992). "Cytokine Dysregulation and Acute Graft-Versus-Host Disease." Blood, vol. 80, No. 12: pp. 2964-2968.
Anderson, P. et al. (1988). "Crosslinking CD3 with CD2 Using Sepharose-Immobilized Antibodies Enhances T Lymphocyte Proliferation." Cellular Immunology, vol. 115, No. 2: pp. 246-256.

Asselin-Paturel et al. (1998). "Quantitative Analysis of Th1, Th2 and TGF-ß1 Cytokine Expression in Tumor, TIL and PBL of Non-Small Cell Lung Cancer Patients." Int. J. Cancer, vol. 77, No. 1: pp. 7-12.
Bachmann, M. F. et al. (1997). "Distinct Roles for LFA-1 and CD28 During Activation of Naive T Cells: Adhesion Versus Costimulation." Immunity, vol. 7, No. 4: pp. 549-557.
Banu, N. et al. (1999). "TGF-ß1 down-regulates induced expression of both class II MHC and B7-1 on primary murine renal tubular epithelial cells." Kidney International, vol. 56, No. 3: pp. 985-994.
Baroja, M.L. et al. (1989). "The Anti-T Cell Monoclonal Antibody 9.3 (Anti-CD28) Provides a Helper Signal and Bypasses the Need for Accessory Cells in T Cell Activation with Immobilized Anti-CD3 and Mitogens." Cellular Immunology, vol. 120, No. 1: pp. 205-217.
Baxevanis, C. N. et al. (2000). "Compromised anti-tumor responses in tumor necrosis factor-α knockout mice." Eur. J. Immunol., vol. 30, No. 7: pp. 1957-1966.
Belardelli, F. et al. (2002). "Cytokines as a link between innate and adaptive antitumor immunity." Trends in Immunology, vol. 23 No. 4: pp. 201-208.
Blazar, B. R. et al. (1997). "Recent advances in graft-versus-host disease (GVHD) prevention." Immunological Reviews, vol. 157: pp. 79-109.
Blazar, B. R. et al. (1998). "Rapamycin Inhibits the Generation of Graft-Versus-Host Disease- and Graft-Versus-Leukemia-Causing T Cells by Interfering with the Production of Th1 or Th1 Cytotoxic Cytokines." Journal of Immunology, vol. 160, No. 11: pp. 5355-5365.
Carayol, G. et al. (1997). "Quantitative Analysis of T Helper 1, T Helper 2, and Inflammatory Cytokine Expression in Patients After Allogeneic Bone Narrow Transplantation: Relationship with the Occurrence of Acute Graft-Versus-Host Disease." Transplantation, vol. 63, No. 9: pp. 1307-1313.
Carpentier, A. F., G. Auf, et al. (2003). "CpG-oligonucleotides for cancer immunotherapy : review of the literature and potential applications in malignant glioma." Front Biosci 8: E115-27.
Chambers, C. A. et al. (1999). "Costimulatory regulation of T cell function." Current Opinion in Cell Biology, vol. 11, No. 2: pp. 203-210.
Champlin, R., I. Khouri, et al. (1999). "Allogeneic hematopoietic transplantation as adoptive immunotherapy. Induction of graft-versus-malignancy as primary therapy." Hematol Oncol Clin North Am 13(5): 1041-57, vii-viii.
Champlin, R., K. van Besien, et al. (2000). "Allogeneic hematopoietic transplantation for chronic lymphocytic leukemia and lymphoma: potential for nonablative preparative regimens." Curr Oncol Rep 2(2): 182-91.
Chang, J. W., M. Peng, et al. (2000). "Induction of Th1 response by dendritic cells pulsed with autologous melanoma apoptotic bodies." Anticancer Res 20(3A): 1329-36.
Chen, Q. et al. (1994). "Production of IL-10 by Melanoma Cells: Examination of its Role in Immunosuppression Mediated by Melanoma." Int. J. Cancer, vol. 56, No. 5: pp. 755-760.
Childs, R. et al. (2002). "Nonmyeloablative Stem Cell Transplantation for Solid Tumors: Expanding the Application of Allogeneic Immunotherapy." Seminars in Hematology, vol. 39, No. 1: pp. 63-71.
Childs, R. et al. (2000). "Regression of metastatic renal-cell carcinoma after nonmyeloablative allogeneic peripheral-blood stem-cell transplantation." The New England Journal of Medicine, vol. 343, No. 11: pp. 750-758.
Childs, R. W. (2000). "Nonmyeloablative allogeneic peripheral blood stem-cell transplantation as immunotherapy for malignant diseases." Cancer J 6(3): 179-87.
Childs, R. W. (2002). "Immunotherapy of solid tumors: nonmyeloablative allogeneic stem cell transplantation." MedGenMed 4(3): 13.
Clerici, M. et al. (1993). "A TH1-->TH2 switch is a critical step in the etiology of HIV infection." Immunology Today, vol. 14, No. 3: pp. 107-111.
Cohen, P. A., L. Peng, et al. (2000). "CD4+ T cells in adoptive immunotherapy and the indirect mechanism of tumor rejection." Crit Rev Immunol 20(1): 17-56.

(56) References Cited

OTHER PUBLICATIONS

Damle, N.K. et al. (1989). "Stimulation Via the CD3 and CD28 Molecules Induces Responsiveness to IL-4 in CD4 +CD29+CD45R- Memory T Lymphocytes." The Journal of Immunology, vol. 143, No. 6: pp. 1761-1767.
Das, H., S. Imoto, et al. (2001). "Kinetic analysis of cytokine gene expression in patients with GVHD after donor lymphocyte infusion." Bone Marrow Transplant 27(4): 373-80.
Daubener, W. et al. (1995). "Establishment of T-helper type 1- and T-helper type 2-like human Toxoplasma antigen-specific T-cell clones." Immunology, vol. 86, No. 1: pp. 79-84.
Deeths, M. J. et al. (1999). "CD8+ T Cells Become Nonresponsive (Anergic) Following Activation in the Presence of Costimulation." The Journal of Immunology, vol. 163, No. 1: pp. 102-110.
De Vita, F., M. Orditura, et al. (2000). "Serum interleukin-10 is an independent prognostic factor in advanced solid tumors." Oncol Rep 7(2): 357-61.
De Waal Malefyt, R. et al. (1993). "Direct Effects of IL-10 on Subsets of Human CD4+ T Cell Clones and Resting T Cells. Specific Inhibition of IL-2 Production and Proliferation." The Journal of Immunology, vol. 150, No. 11: pp. 4754-4765.
D'Orazio, T. J. et al. (1998). "A Novel Role for TGF-ß and IL-10 in the Induction of Immune Privilege." The Journal of Immunology, vol. 160, No. 5: 2089-2098.
Dudley, M. E. et al. (2002). "Cancer Regression and Autoimmunity in Patients After Clonal Repopulation with Antitumor Lymphocytes." Science, vol. 298, No. 5594: pp. 850-854.
Egeter, O. et al. (2000). "Eradication of Disseminated Lymphomas with CpG-DNA Activated T Helper Type 1 Cells from Nontransgenic Mice." Cancer Research, vol. 60, No. 6: 1515-1520.
Eibl, B. et al. (1996). "Evidence for a Graft-Versus-Tumor Effect in a Patient Treated With Marrow Ablative Chemotherapy and Allogeneic Bone Marrow Transplantation for Breast Cancer." Blood, vol. 88, No. 4: pp. 1501-1508.
Elsasser-Beile, U. et al. (1999). "Semiquantitative analysis of Th1 and Th2 cytokine expression in CD3+, CD4+, and CD8+ renal-cell-carcinoma-infiltrating lymphocytes." Cancer Immunol Immunother, vol. 48, No. 4: pp. 204-208.
Emori, Y., H. Sasaki, et al. (1996). "Effect of Z-100, an immunomodulator extracted from human type tubercle bacilli, on the pulmonary metastases of Lewis lung carcinoma in attempt to regulate suppressor T cells and suppressor factor, IL-4." Biotherapy 9(4): 249-56.
Ertl, B., F. Heigl, et al. (2000). "Lectin-mediated bioadhesion: preparation, stability and caco-2 binding of wheat germ agglutinin-functionalized Poly(D,L-lactic-co-glycolic acid)-microspheres." J Drug Targt 8(3): 173-84.
Fan, X. G., W. E. Liu, et al. (1998). "Circulating Th1 and Th2 cytokines in patients with hepatitis C virus infection." Mediators Inflamm 7(4): 295-7.
Finke, J. H., P. Rayman, et al. (1992). "Characterization of a human renal cell carcinoma specific cytotoxic CD8+ T cell line." J Immunother 11(1): 1-11.
Finke, J. H., P. Rayman, et al. (1994). "Characterization of tumor-infiltrating lymphocyte subsets from human renal cell carcinoma: specific reactivity defined by cytotoxicity, interferon-gamma secretion, and proliferation." J Immunother Emphasis Tumor Immunol 15(2): 91-104.
Flanagan, D. L. et al. (1999). "Th1 Cytokines and NK Cells Participate in the Development of Murine Syngeneic Graft-Versus-Host Disease." The Journal of Immunology, vol. 163, No. 3: pp. 1170-1177.
Fowler, D. H., J. Breglio, et al. (1996). "Allospecific CD4+, Th1/Th2 and CD8+, Tc1/Tc2 populations in murine GVL: type I cells generate GVL and type II cells abrogate GVL." Biol Blood Marrow Transplant 2(3): 118-25.
Fowler, D. H. and R. E. Gress (2000). "Th2 and Tc2 cells in the regulation of GVHD, GVL, and graft rejection: considerations for the allogeneic transplantation therapy of leukemia and lymphoma." Leuk Lymphoma 38(3-4): 221-34.
Frassoni, F., M. Labopin, et al. (1996). "Results of allogeneic bone marrow transplantation for acute leukemia have improved in Europe with time—a report of the acute leukemia working party of the European group for blood and marrow transplantation (EBMT)." Bone Marrow Transplant 17(1): 13-8.
Freeman, G. J. et al. (2002). "Protect the killer: CTLs need defenses against the tumor." Nature Medicine, vol. 8, No. 8: pp. 787-789.
Friess, H., H. G. Beger, et al. (1996). "Treatment of advanced pancreatic cancer with mistletoe: results of a pilot trial." Anticancer Res 16(2): 915-20.
Fujimoto, T. et al. (1997). "Streptococcal Preparation OK-432 is a Potent Inducer of IL-12 and a T Helper Cell 1 Dominant State." The Journal of Immunology, vol. 158, No. 12: pp. 5619-5626.
Fujisao, S. et al. (1998). "Th1/Th2 balance alteration in the clinical course of a patient with pure red cell aplasia and thymoma." British Journal of Haematology, vol. 103, No. 2: pp. 308-310.
Gabrilovich, D. I. et al. (1996). "Dendritic Cells in Antitumor Immune Responses. II. Dendritic Cells Grown from Bone Marrow Precursors, but Not Mature DC from Tumor-Bearing Mice, Are Effective Antigen Carriers in the Therapy of Established Tumors." Cellular Immunology, vol. 170, No. 1: pp. 111-119.
Gale, R. P. et al. (1984). "How Does Bone-Marrow Transplantation Cure Leukaemia?" The Lancet, vol. 2, No. 8393: pp. 28-30.
Garlie, N.K., A.V. LeFever, et al. (1999). "T cells coactivated with immobilized anti-CD3 and anti-CD28 as potential immunotherapy for cancer." J Immunother 22(4): 336-45.
Yashiro-Ohtani, Y. et al. (2000). "Non-CD28 Costimulatory Molecules Present in T Cell Rafts Induce T Cell Costimulation by Enhancing the Association of TCR with Rafts." The Journal of Immunology, vol. 164, No. 3: pp. 1251-1259.
Yoon, T. J. et al. (1998). "Prophylactic effect of Korean mistletoe (Viscum album coloratum) extract on tumor metastasis is mediated by enhancement of NK cell activity." International Journal of Immunopharmacology, Vo. 20, No. 4-5: pp. 163-172.
Zitvogel, L. et al. (1996). "Therapy of Murine Tumors with Tumor Peptide-Pulsed Dendritic Cells: Dependence on T Cells, B7 Costimulation, and T Helper Cell 1-associated Cytokines." Journal of Experimentive Medicine, vol. 183, No. 1: pp. 87-97.
Agrewala et al. "Delivery of antigen in allogeneic cells preferentially generates CD4+Th1 cells", Clinical and Experimental Immunology, 2003, vol. 134, pp. 13-22.
Dinauer et al.: "Selective Targeting of Antibody-Conjugated Nanoparticles to Leukemic Cells and Primary T- Lymphocytes", Biomaterials, vol. 26, No. 29, Oct. 2005, pp. 5898-5906.
Encke et al., "Prophylactic and therapeutic vaccination with dendritic cells against hepatitis C virus infection", Clinical and Experimental Immunology, 2005, vol. 142, pp. 362-269.
Fowler et al. "Donor lymphoid cells of TH2 cytokine phenotype reduce lethal graft versus host disease and facilitate fully allogeneic cell transfers in sublethally irradiated mice." Prog Clin Biol Res, 1994, vol. 389, pp. 533-540.
Gong et al., "Fusions of human ovarian carcinoma cells with autologous or allogeneic dendritic cells induce antitumor immunity", The Journal of Immunology, 2000, vol. 165, pp. 1705-1711.
Har-Noy, "Completely mismatched allogeneic CD3/CD28 cross-linked Th1 memor cells elicit anti-leukemia effects in unconditioned hosts without GVHD toxicity", 2008, Leukemia Research, vol. 32, No. 12, pp. 1903-1913.
Meier et al: "Development of a Latex Conjugated Immuno Cytological Marker for Scanning Electron Microscopic Analysis of Quail Chick Chimeras", Journal of Experimental Zoology, vol. 224, No. 1, 1982, pp. 25-38.
Sinha et al.: "Biodegradable Microspheres for Protein Delivery", Journal of Controlled Release, vol. 90, No. 3, Jul. 31, 2003, pp. 261-280.
Office Action issued in corresponding Japanese Patent Application No. 2014-509386 dated Mar. 15, 2016.
Office Action issued in corresponding Japanese Patent Application No. 2014-509386 dated Jul. 4, 2017.
"For T helper type I, II type immune response control therapy using dendritic cells" Journal of Saitama Medical University, 2006, 33(3,4) pp. 67-72 with machine translation.

(56) References Cited

OTHER PUBLICATIONS

Office Action issued in corresponding Canadian Patent Application No. 2,838,046 dated Oct. 15, 2019.
Geppert, T.D. et al. (1988). "Activation of T Lymphocytes by Immobilized Monoclonal Antibodies to CD3, Regulatory Influences of Monoclonal Antibodies to Additional T Cell Surface Determinants." J. Clin. Invest., vol. 81: pp. 1497-1505.
Ghosh, P., K. L. Komschlies, et al. (1995). "Gradual loss of T-helper 1 populations in spleen of mice during progressive tumor growth." J Natl Cancer Inst 87(19): 1478-83.
Gorelik, L., A. Prokhorova, et al. (1994). "Low-dose melphalan-induced shift in the production of a Th2-type cytokine to a Th1-type cytokine in mice bearing a large MOPC-315 tumor." Cancer Immunol Immunother 39(2): 117-26.
Grakoui, A. et al. (1999). "The Immunological Synapse: A Molecular Machine Controlling T Cell Activation." Science, vol. 285, No. 5425: pp. 221-227.
Granucci, F. et al. (2001). "Transcriptional reprogramming of dendritic cells by differentiation stimuli." Eur J Immunol, vol. 31, No. 9: pp. 2539-2546.
Grigg, A., P. Bardy, et al. (1999). "Fludarabine-based non-myeloablative chemotherapy followed by infusion of HLA-identical stem cells for relapsed leukaemia and lymphoma." Bone Marrow Transplant 23(2): 107-10.
Grohmann, U., M. C. Fioretti, et al. (1998). "Dendritic cells, interleukin 12, and CD4+ lymphocytes in the initiation of class I-restricted reactivity to a tumor/self peptide." Crit Rev Immunol 18(1-2): 87-98.
Hara, I., H. Hotta, et al. (1996). "Rejection of mouse renal cell carcinoma elicited by local secretion of interleukin-2." Jpn J Cancer Res 87(7): 724-9.
Heine, G. et al. (2002). "A shift in the Th(1)/Th(2) ratio accompanies the clinical remission of systemic lupus erythematosus in patients with end-stage renal disease." Nephrology Dialysis Transplantion, vol. 17, No. 10: pp. 1790-1794.
Heniford, B. T. et al. (1994). "Interleukin-8 Suppresses the Toxicity and Antitumor Effect of Interleukin-2." Journal of Surgical Research, vol. 56, No. 1: pp. 82-88.
Herlyn, D. and B. Birebent (1999). "Advances in cancer vaccine development." Ann Med 31(1): 66-78.
Horiguchi, S. et al. (1999). "Primary Chemically Induced Tumors Induce Profound Immunosuppression Concomitant with Apoptosis and Alterations in Signal Transduction in T Cells and NK Cells." Cancer Research, vol. 59, No. 12: pp. 2950-2956.
Inagawa, H., T. Nishizawa, et al. (1998). "Mechanisms by which chemotherapeutic agents augment the antitumor effects of tumor necrosis factor: involvement of the pattern shift of cytokines from Th2 to Th1 in tumor lesions." Anticancer Res 18(5D): 3957-64.
Ito, N. et al. (1999). "Lung Carcinoma: Analysis of T Helper Type 1 and 2 Cells and T Cytotoxic Type 1 and 2 Cells by Intracellular Cytokine Detection with Flow Cytometry." Cancer, vol. 85, No. 11: pp. 2359-2367.
Janes, P. W. et al. (1999). "Aggregation of Lipid Rafts Accompanies Signaling Via the T Cell Antigen Receptor." The Journal of Cell Biology, vol. 147, No. 2: pp. 447-461.
Jung, U. et al. (Nov. 2003). "CD3/CD28-costimulated T1 and T2 subsets: differential in vivo allosensitization generates distinct GVT and GVHD effects." Blood, vol. 1, No. 9: pp. 3439-3446.
Kadowaki, N. et al. (2002). "Natural Type I Interferon-Producing Cells as a Link Between Innate and Adaptive Immunity." Human Immunology, vol. 63, No. 12: pp. 1126-1132.
Kai, S. and H. Hara (2003). "Allogeneic hematopoietic stem cell transplantation." Therap Apher Dial 7(3): 285-91.
Kasakura, S. (1998). "[A role for T-helper type 1 and type 2 cytokines in the pathogenesis of various human diseases]." Rinsho Byori 46(9): 915-21.
Kitahara, S., M. Ikeda, et al. (1996). "Inhibition of head and neck metastatic and/or recurrent cancer by local administration of multi-cytokine inducer OK-432." J Laryngol Otol 110(5): 449-53.
Knoefel, B., K. Nuske, et al. (1997). "Renal cell carcinomas produce IL-6, IL-10, IL-11, and TGF-beta 1 in primary cultures and modulate T lymphocyte blast transformation." J Interferon Cytokine Res 17(2): 95-102.
Kobayashi, M. et al. (1998). "A Pathogenic Role of Th2 Cells and Their Cytokine Products on the Pulmonary Metastasis of Murine B16 Melanoma." The Journal of Immunology, vol. 160, No. 12: pp. 5869-5873.
Kobayashi, M., R. B. Pollard, et al. (1997). "Inhibition of pulmonary metastasis by Z-100, an immunomodulatory lipid-arabinomannan extracted from Mycobacterium tuberculosis, in mice inoculated with B16 melanoma." Anticancer Drugs 8(2): 156-63.
Lahn, M. et al. (1999). "Pro-Inflammatory and T Cell Inhibitory Cytokines Are Secreted at High Levels in Tumor Cell Cultures of Human Renal Cell Carcinoma." European Urology, vol. 35, No. 1: pp. 70-80.
Langenkamp, A. et al. (2000). "Kinetics of dendritic cell activation: impact on priming of TH1, TH2 and nonpolarized T cells." Nature Immunology, vol. 1, No. 4: 311-316.
Laux, I. et al. (2000). "Response Differences between Human CD4(+) and CD8(+) T-Cells during CD28 Costimulation: Implications for Immune Cell-Based Therapies and Studies Related to the Expansion of Double-Positive T-Cells during Aging." Clinical Immunology, vol. 96, No. 3: pp. 187-197.
Le Bon, A. et al. (2002). "Links between innate and adaptive immunity via type I interferon." Current Opinion Immunology, vol. 14, No. 4: pp. 432-436.
Lee, P. P. et al. (1997). "T Helper 2-Dominant Antilymphoma Immune Response Is Associated With Fatal Outcome." Blood, vol. 90, No. 4: pp. 1611-1617.
Levine, B.L. et al. (1997). "Effects of CD28 Costimulation on Long-Term Proliferation of CD4+ T Cells in the Absence of Exogenous Feeder Cells." The Journal of Immunology, vol. 159, No. 12: pp. 5921-5930.
Li, L. et al. (1998). "Cyclophosphamide Given After Active Specific Immunization Augments Antitumor Immunity by Modulation of Th1 Commitment of CD4+ T Cells." Journal of Surgical Oncology, vol. 67, No. 4: pp. 221-227.
Liebowitz, D.N. et al. (1998). "Costimulatory approaches to adoptive immunotherapy." Current Opinion Oncology, vol. 10, No. 6: pp. 533-541.
Lowes, M. A., G. A. Bishop, et al. (1997). "T helper 1 cytokine mRNA is increased in spontaneously regressing primary melanomas." J Invest Dermatol 108(6): 914-9.
Ludviksson, B. R. et al. (2000). "The effect of TGF-ß1 on immune responses of naive versus memory CD4+ Th1/Th2 T cells." Eur J Immunol, vol. 30, No. 7: pp. 2101-2111.
Lum, L.G. et al (2001). "Immune modulation in cancer patients after adoptive transfer of ani-CD3/anti-CD28-costimulated T-cells—phase I clinical trial." Journal of Immunotherapy, vol. 24, No. 5: pp. 408-419.
Ma, J. et al. (1998). "Use of encapsulated single chain antibodies for induction of anti-idiotypic humoral and cellular immune responses." Journal of Pharmaceutical Sciences, Vo. 87, No. 11: pp. 1375-1378.
Maeurer, M. J., D. M. Martin, et al. (1995). "Host immune response in renal cell cancer: interleukin-4 (IL-4) and IL-10 mRNA are frequently detected in freshly collected tumor-infiltrating lymphocytes." Cancer Immunol Immunother 41(2): 111-21.
Maus, M. V. et al. (2002). "Ex vivo expansion of polyclonal and antigen-specific cytotoxic T lymphocytes by artificial APCs expressing ligands for the T-cell receptor, CD28 and 4-1BB." Nature Biotechnology, vol. 20, No. 2: pp. 143-148.
Menetrier-Caux, C. et al. (1999). "Renal cell carcinoma induces interleukin 10 and prostaglandin E2 production by monocytes." British Journal of Cancer, vol. 79, No. 1: pp. 119-130.
Moran, M. et al. (1998). "Engagement of GPI-Linked CD48 Contributes to TCR Signals and Cytoskeletal Reorganization: A Role for Lipid Rafts in T Cell Activation." Immunity, vol. 9, No. 6: pp. 787-796.
Muller, M. et al. (2003). "Surface modification of PLGA microspheres." Journal of Biomedic Material Research, vol. 66A, No. 1: pp. 55-61.

(56) References Cited

OTHER PUBLICATIONS

Nabioullin, R. et al. (1994). "Interleukin-10 is a potent inhibitor of tumor cytotoxicity by human monocytes and alveolar macrophages." Journal of Leukocyte Biology, vol. 55, No. 4: pp. 437-442.

Nakagomi, H. et al. (1995). "Lack of Interleukin-2 (IL-2) Expression and Selective Expression of IL-10 mRNA in Human Renal Cell Carcinoma." Int. Journal of Cancer, vol. 63, No. 3: pp. 366-371.

Nishimura, T. et al. (2000). "The critical role of Th1-dominant immunity in tumor immunology." Cancer Chemother Pharmacol, vol. 46 (Suppl): S52-S61.

Nitta, T., M. Hishii, et al. (1994). "Selective expression of interleukin-10 gene within glioblastoma multiforme." Brain Res 649(1-2): 122-8.

O'Donnell P.B. et al. (1997). "Preparation of microspheres by the solvent evaporation technique." Advanced Drug Delivery Reviews, vol. 28, No. 1: pp. 25-42.

Oka, H. et al. (1999). "An immunomodulatory arabinomannan extracted from Mycobacterium tuberculosis, Z-100, restores the balance of Th1/Th2 cell responses in tumor bearing mice." Immunology Letters, vol. 70, No. 2: pp. 109-117.

Okamoto, T. et al. (1997). "Local Injection of OK432 Can Augment the TH1-Type T-Cell Response in Tumor-Draining Lymph Node Cells and Increase Their Immunotherapeutical Potential." International Journal of Cancer, vol. 70, No. 5: pp. 598-605.

Okutomi, T., Y. Kato, et al. (2000). "[Clinical effects of adjuvant therapy using Z-100 (Ancer 20 injection) for oral cancer—prevention of stomatitis and hematopoietic impairment]." Gan To Kagaku Ryoho 27(1): 65-71.

Onishi, T. et al. (1999). "An assessment of the immunological environment based on intratumoral cytokine production in renal cell carcinoma." BJU International, vol. 83, No. 4: pp. 488-492.

Raghupathy, R. (1997). "Th1-type immunity is incompatible with successful pregnancy." Immunology Today, vol. 18, No. 10: pp. 478-482.

Extended European Search Report for EP Patent Application No. 12779711.6, dated Jan. 23, 2015.

Shu U et al. (1995) "Activated T cells induce IL-12 release from monocytes via CD40-CD40 ligand interaction", Journal of Allergy and Clinical Immunology, vol. 95, No. 1, pt. 2, p. 361, Abstract.

Zabala, M. et al. (2004). "Optimization of the Tet-on System to Regulate Interleukin 12 Expression in the Liver for the Treatment of Hepatic Tumors". Cancer Res., Apr. 15, 2004; 64(8): 2799-804.

International Search Report and Written Opinion; PCT/US2012/036123, dated Oct. 11, 2012.

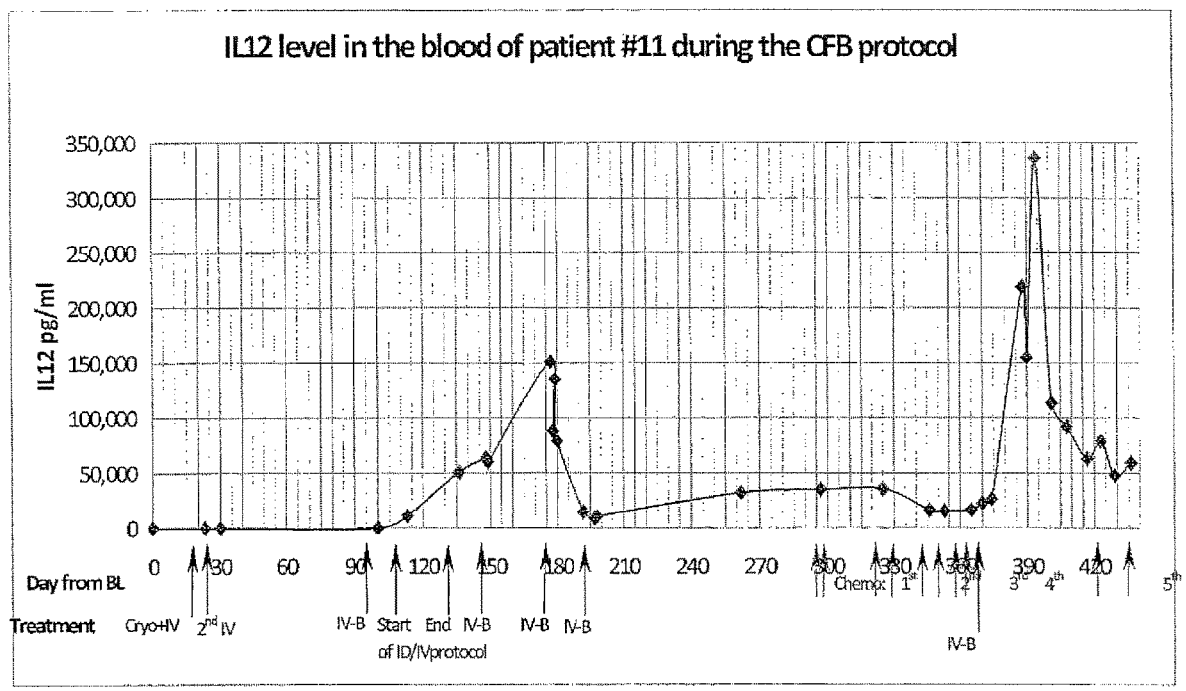

INDUCTION OF IL-12 USING IMMUNOTHERAPY

CROSS-REFERENCE TO RELATED APPLICATION

This Application is a divisional of U.S. patent application Ser. No. 14/962,728, filed Dec. 8, 2015, which is a divisional of U.S. patent application Ser. No. 13/581,745, filed Nov. 9, 2012, which is a Section 371 National Stage Application of International Application No. PCT/US2012/036123, filed May 2, 2012, in English, which claims priority to U.S. provisional patent application Ser. No. 61/482,009, filed May 3, 2011, U.S. provisional patent application Ser. No. 61/528,484, filed Aug. 29, 2011, U.S. provisional patent application Ser. No. 61/564,551, filed Nov. 29, 2011 and U.S. provisional patent application Ser. No. 61/582,881, filed Jan. 4, 2012, the contents of each are hereby incorporated by reference in their entirety.

FIELD

This invention relates to therapy using immune cells. More specifically, this invention relates to immune cell therapy that promotes IL-12 production in patients.

BACKGROUND

The most precise, powerful and safest disease prevention and treatment mechanism known is the natural 'sterilizing' immune response which combines elements of both innate and adaptive immunity to clear the body of a large variety of foreign pathogens without medical intervention. The immune system is designed to 'remember' the cleared foreign antigens in order to quickly mount an immune response upon re-infection. Immune systems, even those of cancer patients, can recognize and mount a response to foreign antigens, such as found on viruses and bacteria, sufficiently enough to completely destroy and eliminate them from the body. The ferocity and specificity of this sterilizing immune response can be witnessed in the manner in which an inadequately suppressed immune system can completely destroy large transplanted organs, such as a kidney, liver or heart, while sparing self tissues. The destructive effect of this immunity against foreign antigens would be beneficial if this effect could be redirected to tumors and/or other antigens that escape due to an insufficient immune response by the patient.

Immunotherapy is dedicated to developing methods to harness, direct and control the immune response against a variety of infectious and noninfectious diseases including cancer. Therapeutic vaccines are a type of immunotherapy designed to educate the immune system. In patients with existing cancers, the vaccines are designed so the patient's immune system recognizes the tumor cells as foreign. If tumors are recognized by the immune system as a foreign pathogen, an immune response could theoretically be elicited which could cause immune cells to destroy large tumors and seek out and destroy metastatic tumor cells wherever they reside in the body. After successful immunotherapy, the ability of the immune system to 'remember' eliminated foreign cells would enable the immune system to eliminate any recurrent cancer cells without any additional treatment, much like the immune system protects against opportunistic infections.

An individual's immune system response to diseases or to disease organisms can be either a Th1 response or Th2 response. In a Th1 response, the CD4+ T cells become polarized toward Th1 cells and conversely, in a Th2 response, the CD4+ T cells become polarized toward Th2 cells. This increasingly popular classification method is referred to as the Th1/Th2 balance. Th1 cells promote cell-mediated immunity, while Th2 cells induce humoral immunity. Cellular immunity (Th1) directs natural killer cells (NK), T-cells and macrophages to attack abnormal cells and microorganisms at sites of infection. Humoral immunity (Th2) results in the production of antibodies used to neutralize foreign invaders. In general, Th2 polarization of CD4+ T cells has been shown to relate to cancer progression in most human and animal cancer studies, while Th1 polarization is correlated with tumor regression and anti-tumor immunity.

The immune response of an individual, Th1/Th2 balance, can be evaluated through the balance of cytokines in the individual. Cytokines are small cell-signaling protein molecules. The term cytokine is used as a generic name for a diverse group of soluble proteins and peptides that act as regulators normally at nano- to picomolar concentrations and which, either under normal or pathological conditions, modulate the functional activities of individual cells and tissues. These proteins also mediate interactions between cells directly and regulate processes taking place in the extracellular environment. Interleukins are a group of cytokines involved in immunomodulation and can be synthesized by a variety of cells in the immune system. There are a number of interleukins, such as IL-2, IL-4, IL-10 and IL-12, and each of these interleukins has a specific role within the immune system.

Th1 cells produce Type 1 cytokines that are involved in inflammatory responses. Type 1 cytokines include, for example, IL-2, IL-12, IL-15, IFN-gamma, TNF-alpha, TNF-beta, GM-CSF and C-C chemokines. Th2 cells produce Type 2 cytokines that are involved in humoral immune responses. Type 2 cytokines include, for example, IL-4, IL-5, IL-6, IL-10, IL-13 and TGF-beta. Th1 and Th2 immune responses are counter-regulatory, such that increased Type 1 responses downregulate Type 2 responses and increased Type 2 responses downregulate Type 1 responses.

IL-12 is a heterodimer composed of a p35 and a p40 subunit. It is produced primarily by Antigen Presenting Cells (APC). IL-12 can also be produced by monocytes and macrophages, dendritic cells and B-cells. IL-12 exerts immunomodulatory effects on T-cells and natural killer cells. Endogenous IL-12 is known to be involved in generating optimal Th1 responses and can play an important role in cell-mediated immunity against intracellular pathogens.

IL-12 has been the subject of intense investigation because it modulates important components of the immune system and has been demonstrated to have dramatic anti-tumor effects in the laboratory and in animal studies. IL-12 has been implicated, for example, in inhibiting growth of human lung adenocarcinoma and acute myeloid leukemia. However, the use of exogenous IL-12 in a therapeutic regimen has been limited by high toxicity in humans.

BRIEF DESCRIPTION OF THE DRAWINGS

FIG. 1 is a graph illustrating the IL-12 level in a patient's plasma over more than a year. Allogeneic, activated Th-1 cells were administered to the patient at various times using various modes of administration.

DETAILED DESCRIPTION OF ILLUSTRATIVE EMBODIMENTS

The present invention relates to compositions and methods that lead to detectable levels of IL-12 in the plasma of a patient. The present invention includes a composition that, when administered to a patient, can lead to the production of detectable levels of endogenous IL-12 in the patient's plasma, without any significant toxicity. The endogenous IL-12 can surprisingly be detected in patients with cancer. The composition preferably includes allogeneic activated T-cells. T-cells are not capable of producing IL-12, therefore the T-cell composition administered to the patient elicits the production of IL-12 by the patient's own APC.

The present invention also includes methods of inducing production of endogenous IL-12 in a patient by the patient's own immune system. The method includes administering a composition of allogeneic material, preferably allogeneic activated T-cells. The composition may be administered as a single dose or multiple doses. Preferably, the allogeneic activated T-cells are administered in frequent, low doses. The allogeneic cells can be administered by intradermal, intravenous or intralesional routes. Preferably, the frequency is not less than every 3 days. When these compositions are administered, the patient's own immune system can be induced to produce detectable levels of endogenous IL-12 in the plasma, even in a patient with a cancer. Generally, IL-12 is not found in patients with cancer because tumors can inhibit expression of IL-12. Surprisingly, the methods described herein can overcome this inhibition and create an environment sufficient to induce expression of IL-12 in the plasma for extended periods of time, for example, several months or even a year. Furthermore, the presence of endogenous IL-12 in plasma does not lead to significant toxicity in the patient as does the administration of exogenous IL-12 as medicant.

By endogenous IL-12, it is meant that the IL-12 is synthesized in the patient by the patient's own immune system. Specifically, the IL-12 can be synthesized by the patient's antigen presenting cells (APC). APC can include monocytes and macrophages, dendritic cells and B-cells. By exogenous IL-12, it is meant that the IL-12 is not synthesized by the patient's own immune system. Exogenous IL-12 includes IL-12 isolated and/or purified IL-12 from another individual or IL-12 that is expressed by a DNA construct(s) that includes a gene for IL-12.

Advantageously, the systemic production of endogenous IL-12 in the patient leads to minimal or no toxicity to the patient. The patient may experience transient symptoms such as transient flu-like symptoms. Generally, when exogenous IL-12 has been administered to the patient, toxic effects have limited the use in a therapeutic setting. The ability of the methods described herein to promote endogenous production of IL-12 that can lead to systemically detectable levels of IL-12 in the plasma without toxicity is surprising. This result enables the use of the patient's own immune system to harness the benefits created from the presence of IL-12 toward reduction and/or elimination of tumors and cancerous cells.

The use of these methods can also be applicable to reduction and/or elimination of other diseases that respond favorably to a Th1 environment, specifically to IL-12. Such diseases include cancer, infectious diseases, including chronic viral and intracellular bacterial or mycobacterial diseases, such as hepatitis B, hepatitis C, HIV1, HIV2, HTLV1, HTLV2, HPV, *Mycobacterium tuberculosis*, periodontal disease, and allergic diseases like atopic asthma. In addition, methods to promote the endogenous production of IL-12 can have an anti-aging effects by maintaining cellular immunity. The balance of Th1 to Th2 cells in normal individuals decreases as part of the aging process, making the elderly more susceptible to infectious diseases and cancer. Promotion of endogenous IL-12 production can increase the Th1/Th2 ratio, thus protecting against vulnerability to disease.

The compositions of the present invention generally include foreign antigens, preferably alloantigens. The compositions also include at least one Th1 cytokine and/or at least one DC effector molecule capable of inducing the maturation of DC to produce IL-12. The therapeutic composition generally includes the at least one Th1 cytokine, and/or the at least one DC effector molecule combined together with the alloantigen. The composition preferably contains living allogeneic activated T-cells that are capable of providing each of the components of the composition in a single cell type. In preferred embodiments, living allogeneic Th1 cells that are activated to produce Th1 cytokines, such as interferon-gamma, tumor necrosis factor-alpha and interleukin-2 and express the DC maturation effector molecule CD40L on the cell surface are used. Alternatively, the three components of the composition could be sourced from more than one cell type. For example, the Th1 cytokines may be sourced from one cell type in a composition and the alloantigen from a separate cell type and the DC effector molecules from a third cell type. Alternatively one cell type could contain any two of the components and a second cell type contain the third. The cell types do not need to be living as long as they provide a source of the necessary components of the composition.

Alternatively, the composition components can be sourced from natural or bioengineered proteins. For example, recombinant or purified Th1 cytokines or DC maturation molecules or alloantigens could be used together or in combination with living cell components. The composition components could be combined on a "chip" or biodegradable platform. The components do not need to be delivered at the same time to a patient, but can be delivered in any sequence.

The alloantigens in the therapeutic compositions must be provided in a manner that the antigen can be engulfed or presented to the immune system in order to be processed and presented to T-cells. The antigen can be a natural part of living cells or can be altered or bioengineered using molecular biological techniques. The antigen can be soluble or immobilized on a surface, an intact part of a living organism or cell, or a part of an attenuated organism. In preferred embodiments, the alloantigens are allogeneic T-cells and in more preferred embodiments, allogeneic activated T-cells.

In one exemplary embodiment, the therapeutic composition includes alloantigens expressed on T-cells. The T-cells are preferably CD4+ T-cells, and more preferably Th1 cells. The Th1 cells can be in-vitro differentiated, expanded and activated from naïve CD4+ precursor cells derived from normal blood donors. Preferably, the cells are in an activated state at the time of administration. Preferably, the cells are activated by cross-linking monoclonal antibodies directed to CD3/CD28 surface molecules. Crosslinking is preferably caused by immobilization of the CD3/CD28 monoclonal antibodies on a surface. Preferably, the surface is a micro- or nanabead particle. The beads may be biodegradable beads. These cells can produce large amounts of inflammatory Th1 cytokines and express effector molecules on the cell surface, such as CD40L, which serve to promote the development of Th1 immunity by causing endogenous IL-12 production.

In preferred embodiments, the therapeutic composition includes activated allogeneic Th1 cells. These activated Th1 cells can be powerful inflammatory agents. These activated allogeneic Th1 cells and methods for preparing them are described, for example, in U.S. Pat. Nos. 7,435,592, 7,678, 572, 7,402,431 and 7,592,431 and are incorporated herein by reference. The activated allogeneic Th1 cells are intentionally mismatched to the patient.

A variety of Th1 inflammatory cytokines may be included in the therapeutic compositions. Examples of inflammatory Th1 cytokines include: IL-1, IL-2, IL-6, IL-12, IL-15, IFN-gamma, TNF-alpha, TNF-beta, GM-CSF and C-C chemokines and do not include TGF-beta, IL-4 or IL-10. The cytokine component can be natural or recombinant cytokines or can be bioengineered molecules designed to interact with the receptors for a cytokine. The cytokines may be directly included in the therapeutic compositions. Alternatively, the therapeutic compositions can include living cells or other components that produce and secrete the cytokines. Preferably the cytokines are provided naturally through an activated cell source, as exogenous cytokines tend to be very toxic to patients while endogenous cytokines are not. In some exemplary embodiments, the therapeutic compositions include T-cells in an activated state that are producing and secreting the inflammatory Th1 cytokines and thus, can serve as the source of these cytokines in the therapeutic compositions.

The therapeutic composition can include a factor or factors that cause the maturation of immature DCs. Specifically, maturation factors which promote DC1 cell maturation and IL-12 production leading to interferon-gamma production and Th1 adaptive immunity. DCs are capable of evolving from immature, antigen-capturing cells to mature, antigen-presenting, T cell-priming cells which convert antigens into immunogens and express cytokines, chemokines, costimulatory molecules necessary to initiate an immune response. The types of T cell-mediated immune responses (Th1 vs. Th2) induced varies depending on the activation signals received from the surrounding microenvironment. The ability of DCs to regulate immunity such as anti-tumor and anti-infectious disease immunity is dependent on DC maturation to promote Th1 immunity. Human DCs are not a homogenous population. Besides inducing anti-tumor immunity, DCs can induce anergy or tolerance. DCs originate from CD34+ hematopoietic stem cells (HSC). Myeloid dendritic cells (DC1) and plasmacytoid DCs (DC2) are the two principal subpopulations of human DCs, and their characteristics vary greatly in phenotype, migration, and function. DC1 cells are effective T cell stimulators, inducing a tumor specific immune response. CD11c+DC1 cells primarily induce Th1 differentiation, whereas DC2 cells, which express the receptor for IL-3 (CD123), mainly promote a Th2 response. Both DC populations are significantly lower in patients with cancer than in healthy donors. DC1 cells produce IL-12 upon maturation and DC2 cells produce IL-10.

Production of cytokines such as IL-10 and IL-12 during the DC maturation process influences DC induction of a Th1 or Th2 immune response. In addition to expressing high levels of antigen-presenting molecules and costimulatory molecules, mature DC must release large amounts of IL-12 in order to stimulate a Th1 immune response. Release of IL-10, blocks the DC maturation process by interfering with up-regulation of costimulatory molecules and production of IL-12, subsequently limiting the ability of DCs to initiate a Th1 response.

A variety of factors can induce maturation of DC to become DC1, IL-12 producing cells following antigen uptake and processing, including: whole bacteria or bacterial-derived antigens (e.g. lipopolysaccharide, LPS), inflammatory cytokines such as IFN-gamma, TNF-alpha, IL-1, GM-CSF, ligation of select cell surface receptors (e.g. CD40), viral products (e.g. double-stranded RNA), Fas engagement on immature DCs, for example, induces both maturation and release of IL-1 beta and IFN-gamma. Ligation of CD40 promotes an up-regulation of the costimulatory molecules B7-1/CD80 and B7-2/CD86 and IL-12 secretion and release of chemokines (e.g. IL-8, MIP-1 alpha, MIP-1 beta).

In some preferred embodiments, CD40L is included as a factor for maturation of the DCs. Inclusion of other factors that cause maturation of the DCs is also within the scope of the invention. In some exemplary embodiments, the therapeutic compositions include T-cells in an activated state which express high density CD40L on the surface. CD40L is a potent effector molecule for DC maturation to produce IL-12.

In one exemplary embodiment, the therapeutic composition includes activated allogeneic T-cells, at least one type I cytokine and at least one factor that causes maturation of DCs. Compositions including these components are described, for example, in pending U.S. patent application Ser. No. 12/967,910 filed on Dec. 14, 2010 and incorporated herein by reference.

Intratumoral administration of the therapeutic compositions after ablation of some of the tumor cells in order to release tumor associated antigens into the microenvironment can provide a potent adjuvant effect for the maturation of DC to DC1 phenotype which produces IL-12 and promotes development of Type 1 anti-tumor immunity and the down regulation of tumor immunoavoidance mechanisms. Administration of the therapeutic composition can also be accomplished by other methods including, for example, intravenous, intradermal, intrathecal, intraperitoneal, intralesional, intrapleural administration and the like. Preferably, the composition is first administered intradermally, as the skin is rich in immature DC called Langerhans cells. In the presence of inflammatory Th1 cytokines, such as interferon-gamma, tumor necrosis factor-alpha, IL-2 and GM-CSF and a DC maturation factor, such as CD40L, the Langerhan's cells uptake the alloantigen and mature to DC1, IL-12 producing cells. These mature cells migrate to the lymphnodes and promote development of Th1 immunity.

Intradermal injections of the composition can "prime" a patient to become immune to the alloantigen in the composition. Multiple intradermal injections can increase the number of Th1 memory cells specific for the alloantigens in the circulation of the patient, which in turn changes the Th1/Th2 balance. Injection of $1\times10^6$ cells to $1\times10^7$ allogeneic activated Th1 cells is a preferred intradermal dose, $1\times10^7$ cells in 1 ml of fluid is the most preferred. The intradermal dosing is preferably repeated multiple times in order to build up the number of circulating Th1 memory cells. The intradermal dosing frequency is preferably about 3-4 injections every 7 days, more preferably every 3-4 days.

In preferred embodiments, the intradermal dosing is followed by an intratumoral dosing of the composition to create an in-situ vaccine. The intratumoral dosing is preferably conducted following the in-situ ablation of some of the tumor cells in the target lesion. The ablation is preferably caused by use of extreme cold (cryoablation) or heat (radiation), but can be also done using a variety of methods including alcohol ablation, chemotherapy and/or monoclonal antibody drugs. A preferred intratumoral dose is between about $1\times10^7$ and $1\times10^8$ cells, most preferably about $3\times10^7$ cells. It is preferred that a first intratumoral dose be injected immediately following the ablation and a second within about 7 days, preferably within about 3-4 days following the first injection. This process of ablation followed by intratumoral injection of the composition can be repeated as necessary.

The method also preferably includes administering the composition intravenously in order to cause the activation of host immune cells (both innate and adaptive) and their extravasation to sites of inflammation, including tumor locations. The intravenous dose of the composition of allogeneic activated Th1 cells preferably includes about $1 \times 10^7$ to $1 \times 10^9$ cells, more preferably about $5 \times 10^7$ to $1 \times 10^8$ cells. The intravenous infusions can be repeated several times, preferably on a monthly basis.

The allogeneic Th1 cells of the composition preferably produce large amounts of the Type 1 cytokines: IL2, IFN-γ, TNF-alpha □ and GM-CSF. The presence of inflammatory Th1 cytokines in a microenvironment where immature DC are engulfing and processing antigens can help promote maturation to DC1, IL-12 producing DC. IL-12 can stimulate the level of IFN-γ that in turn can lead to promotion of a Th1 immunity. IFN-γ is a pivotal Type 1 cytokine necessary to promote Type 1 anti-tumor immunity. IFN-γ can mediate anti-tumor effects by directly inhibiting tumor cell growth and inducing T cell-mediated anti-tumor responses. IFN-7 secretion can independently contribute to the NK cell response and enhance the NK cell response activated by IL-12.

The preferred medicament containing activated allogeneic Th1 cells can be derived from precursors purified from normal, screened blood donors. The cells should be supplied as a sterile, low endotoxin dosage form formulated for either intradermal or intratumoral injection, or intravenous infusion. The cells may also be formulated for intraperitoneal, intrapleural or epidural infusions. The donors are preferably tested to be negative for HIV1, HIV2, HTLV1, HTLV2, HBV, HCV, RPR (syphilis), and the cells are preferably tested to be negative for mycoplasma, EBV and CMV. In preferred embodiments, the activated allogeneic cells are HLA mismatched with the patient.

The methods of the present invention generally relate to producing detectable levels of endogenous IL-12 in the patient's plasma. The methods include administering the compositions of the present invention in such a way as to engineer the patient's immune system to produce endogenous IL-12 at detectable levels in the patient's plasma. The methods described herein can increase the circulating numbers of Th1 immune cells in cancer patients, shifting the balance from Th2 environment to a Th1 environment. Additionally, the methods may also include steps that elicit an anti-tumor specific Th1 immunity and/or activate components of the innate and adaptive immune responses to generate a sustained Th1 cytokine environment in order to down-regulate tumor immunoavoidance.

The methods of the present invention can include administering a composition containing a foreign antigen to promote Th1 immunity in the patient against the foreign antigen. The method may also include ablating all or a portion of the tumor that results in at least some tumor necrosis. A variety of methods can be used to generate tumor necrosis in the patient. The method may also involve creating an inflammatory microenvironment in proximity to the site of tumor necrosis, i.e the site of the tumor lesion. In addition, the method can also include activating the adaptive and innate immune cells of the patient to maintain a prolonged Th1 environment. In preferred embodiments, a key component of the method includes the use of a medicament or composition containing activated allogeneic T cells as described above.

Since most human cancer patients generally present with polarized Th2 immunity, the objective of this method of treatment is generally to increase the amount of circulating Th1 cells in cancer patients. The number of circulating Th1 cells can be built up in the cancer patient by administering one of the therapeutic compositions described above to the patient that includes a foreign antigen.

In an exemplary embodiment, the patient is administered activated allogeneic Th1 cells that are injected intradermally. In preferred embodiments, intradermal injections are on a weekly schedule once a week for about 3-4 weeks. In other preferred embodiments, the intradermal injections may be administered multiple times about every 3-4 days. Intradermal injections may be administered every two days or up to a year apart. The injection schedule should be designed to enhance the footprint of Th1 memory cells in circulation. The alloantigens expressed on the foreign cells can stimulate a potent immune rejection response. In addition, the presence of Th1 cytokines in the composition or the expression of Th1 cytokines by the allogeneic cells can provide the inflammatory adjuvant environment necessary to steer the immune response to the alloantigens toward Th1 memory immunity. This can create an increased pool of Th1 memory cells in circulation in the patient specific for the alloantigens contained within the allogeneic Th1 cells. Multiple administrations can act as booster shots, increasing the number of circulating memory Th1 cells specific for the alloantigens.

In some embodiments, the administration of allogeneic activated T cells may be followed by additional steps to enhance the patient response. These steps can include, for example, ablation of the tumor that causes tumor necrosis along with intratumoral administration of additional allogeneic activated T cells. Additional administration of the allogeneic activated cells intravenously may also be performed. These methods are described in the U.S. Pat. No. 7,972,594 to Har-Noy incorporated herein by reference.

The administration of the therapeutic compositions or medicaments using the methods described herein can promote the systemic production of endogenous IL-12 in the patient by the patient's own immune system. The concentration of the endogenous IL-12 in the patient is sufficient that the IL-12 can be detected in the patient's plasma. The detectable levels of IL-12 are endogenous and not a result of any that might be present in the therapeutic composition because generally the components of the composition are eliminated by the patient's immune system in the rejection response elicited by the administration of allogeneic material. In preferred embodiments, the composition contains T-cells which can not produce IL-12. Thus, any of the IL-12 detected in the patient's plasma is a result of the IL-12 produced by the patient's own immune system.

Preferably, the IL-12 is produced by the patient's immune cells, for example, the patient's own monocytes, natural killer cells and dendritic cells. These cells will have matured under the influence of the inflammatory or Type I cytokines generated by the administration of the compositions described herein.

The concentration of the IL-12 in the patient's plasma can vary but is generally at least about 8000 pg/ml. The concentration of the IL-12 in the patient's plasma is preferably between about 8000 pg/ml to 200,000 pg/ml. As described herein, the concentration of the IL-12 detected in the plasma of the patient does not lead to toxicity issues. However, administration of exogenous IL-12 has been known to be toxic to patients. Patients that seroconvert to IL-12 expression in the plasma have an increased survival compared to patients that do not express IL-12 in their serum. The level of IL-12 may not correlate with survival, only the presence of IL-12 is crucial.

The increase in IL-12 is generally detected after a period of time after the administration of the composition. Preferably, after about 3-4 weeks of dosing with therapeutic composition, the IL-12 can be detected in the plasma. There can be a delay in IL-12 seroconversion for about 90-120 days after the administration of the last composition.

The IL-12 in the plasma can be detected by using a variety of methods. IL-12 has two subunits called the p40 and p35 chains and antibodies specific to p40 are preferred for detection. Several methods are available to detect the presence of IL-12. Detection of IL-12 can include, for example, ELISA, and cytokine bead array.

The methods described herein can be suitable for a variety of patients, including humans. The methods may also be used on other mammals.

The present invention also includes methods of treating a disease in a patient. The diseases can include cancerous tumors as described above, hematological malignancies, as well as diseases caused by pathogenic agents. Other diseases that are susceptible to a Th1 response in a patient can also be treated using the methods described herein. The patient is administered the allogeneic composition according to the methods described herein. The patient's plasma is then monitored for the presence of IL-12. The detection of endogenous IL-12 can be indicative of the patient's immune response to the disease. Additional administrations of the therapeutic composition may be performed for maintenance of the IL-12 levels and thereby maintaining the patient's immune response against the disease antigens.

Examples

This study was performed to monitor the level of IL-12 in the plasma of a patient treated with allogeneic, activated Th1 cells. These activated allogeneic Th1 cells and methods for preparing them are described in U.S. Pat. No. 7,435,592. The activated allogeneic Th1 cells were intentionally mismatched to the patient.

Intradermal Injections-Intradermal injections of activated allogeneic Th1 cells were administered. The cells were suspended in 1 ml at a density of 1×10$^7$ cells/ml.

Intratumoral Injections-Intratumoral injection was administered in the necrotic center of an ablated tumor within one hour of ablation.

Cryoablation was done with the use of a CryoCare-28 Percutaneous Probe System (Endocare, Calif., USA). This system used the Joule-Thomson effect to cool the end of a cryoprobe in a closed system. In accordance with the gas coefficient and the dimension of the nozzle, different gaseous elements generate different thermal exchange events at the area close to the nozzle. Argon gas was used for cooling (−187° C.), and helium was used for heating (67° C.).

The planned target tumor lesion was identified and located under CT image guidance. A sterile field was created and local anesthesia administered to the planned probe insertion site. A guide probe was inserted percutaneously and verified by CT to be within the target tumor lesion. One or two freeze-thaw cycles were performed. A single probe of 2- or 5-mm was used according to the size of the target tumor. The time of freezing was approximately 5-20 minutes dependent on the achievement of an "ice-ball", visible on CT. Thawing was achieved by input of helium during a period equivalent to the freezing time before the second freezing process was initiated. The procedure requires ablation of a sample of the tumor lesion and does not require complete tumor ablation with tumor-free margins.

The lesion was allowed to cool following the second freezing cycle before injection of the allogeneic activated Th1 cells.

Tables 1, 2 and 3 show the timing of the specific treatments and the level of IL-12 in the patient's plasma on the indicated days. FIG. 1 is a graph illustrating the IL-12 expression by the patient's immune system during the study.

TABLE 1 pt# 11

| weeks from BL | day from BL | treatment | IL12 pg/ml |
|---|---|---|---|
| 0 | 0 | Base | 0 |
| 3 w + 2 d | 23 | Cryo + IT + IV | 0 |
| 4 w + 2 d | 30 | post-2nd IV | 0 |
| 14 w + 2 d | 100 | post-IV-B | 0 |
| 16 w + 1 d | 113 | pre-1st ID in ID/IV prot. | 11,317 |
|  | 136 | post-3rd IV in ID/IV prot. | 50,725 |
| 21 w + 1 d | 148 | pre-IV-B in ID/IV prot. | 64,117 |
|  | 149 | post-IV-B in ID/IV prot. | 60,301 |
| 25 w + 2 d | 177 | Pre-IV-B 60D IV/ID (T) 14APR10 | 151,048 |
|  | 178 | Post-IV-B 60D (T) 15APR10 | 88,362 |
|  | 179 | 48 h Post-IV-B 60D (T) 16APR10 | 135,169 |
|  | 180 | 72 h Post-IV-B 60D (T) 17APR10 | 79,476 |
| 27 w + 3 d | 192 | F/U | 14,840 |
|  | 197 | Pre-IV-B | 8,867 |
|  | 198 | Post-IV-B | 10,610 |
| 37 w + 3 d | 262 | F/U D240 | 32,188 |
| 42 w + 3 d | 297 | pre-chemo | 35,115 |
| 46 w + 3 d | 325 |  | 35,552 |
| 49 w + 3 d | 346 |  | 16,265 |
| 50 w + 3 d | 353 |  | 15,584 |
| 52 w + 1 d | 365 |  | 16,546 |
| 52 w + 6 d | 370 | Plasma* | 22,626 |

TABLE 2

| treatment | day from BL | IL12 pg/ml |
|---|---|---|
| Base | 0 | 0 |
| Cryo + IT + IV | 23 | 0 |
| post-2nd IV | 30 | 0 |
| post-IV-B | 100 | 0 |
| pre-1st ID in ID/IV prot. | 113 | 11,317 |
| post-3rd IV in ID/IV prot. | 136 | 50,725 |
| pre-IV-B in ID/IV prot. | 148 | 64,117 |
| post-IV-B in ID/IV prot. | 149 | 60,301 |
| Pre-IV-B 60D IV/ID (T) 14APR10 | 177 | 151,048 |
| Post-IV-B 60D (T) 15APR10 | 178 | 88,362 |
| 48 h Post-IV-B 60D (T) 16APR10 | 179 | 135,169 |
| 72 h Post-IV-B 60D (T) 17APR10 | 180 | 79,476 |
| F/U | 192 | 14,840 |
| Pre-IV-B | 197 | 8,867 |
| Post-IV-B | 198 | 10,610 |
| F/U D240 | 262 | 32,188 |
| pre-chemo | 297 | 35,115 |
|  | 325 | 35,552 |
|  | 346 | 16,265 |
|  | 353 | 15,584 |
|  | 365 | 16,546 |
| pre-IV-B | 370 | 22,626 |
| F/U | 374 | 26,405 |
| F/U | 388 | 219,275 |
| F/U | 390 | 155,023 |
| F/U | 394 | 336,141 |
| F/U | 401 | 113,513 |
| F/U | 408 | 92,122 |

TABLE 2-continued

| treatment | day from BL | IL12 pg/ml |
|---|---|---|
| F/U | 417 | 63,357 |
| F/U | 423 | 79,075 |
| F/U | 429 | 48,038 |
| F/U | 436 | 59,471 |

TABLE 3

| Chemo | days from BL | |
|---|---|---|
| 1st | 296 | start |
|  | 301 | stop |
| 2nd | 324 | start |
|  | 331 | stop |
| 3rd | 345 | start |
|  | 352 | stop |
| 4th | 359 | start |
|  | 364 | stop |
| 5th | 408 | start |
|  | 415 |  |
|  | 422 | stop |
| 6th | 436 | start |

Although the present invention has been described with reference to preferred embodiments, workers skilled in the art will recognize that changes may be made in form and detail without departing from the spirit and scope of the invention.

What is claimed is:

1. A method of treating a patient with a solid tumor, the method comprising:
    inducing the production of endogenous IL-12 in the patient, wherein the endogenous IL-12 is induced by administering a composition comprising activated allogeneic Th1 cells to the patient, wherein the Th1 cells are activated by cross-linking CD3 and CD28;
    ablating all or portion of the solid tumor in the patient to generate tissue necrosis along with intratumoral administration of the activated allogeneic Th1 cells;
    measuring the level of endogenous IL-12 in the patient; and
    readministering the composition until endogenous IL-12 in the plasma of the patient is at least about 5000 pg/ml.

2. The method of claim 1, wherein administration of the composition increases the level of IFN-gamma and Th1 response in the patient.

3. The method of claim 1, wherein the method further comprises readministering the composition until the level of endogenous IL-12 in the plasma of the patient is at least about 8000 pg/ml.

* * * * *